United States Patent [19]

Somerville et al.

[11] Patent Number: 5,330,504
[45] Date of Patent: Jul. 19, 1994

[54] CARDIOVERTING DEFIBRILLATING DEVICE WITH OFF-LINE ECG ANALYSIS

[75] Inventors: William M. Somerville, Aspley; John P. Wickham, Five Dock, both of Australia

[73] Assignee: Telectronics Pacing Systems, Inc., Englewood, Colo.

[21] Appl. No.: 56,598

[22] Filed: May 3, 1993

Related U.S. Application Data

[63] Continuation-in-part of Ser. No. 851,624, Mar. 16, 1992, abandoned.

[51] Int. Cl.$^5$ .............................................. A61N 1/39
[52] U.S. Cl. ........................................................ 607/5
[58] Field of Search .................. 607/14, 4, 5; 128/697

[56] References Cited

U.S. PATENT DOCUMENTS

| | | |
|---|---|---|
| 3,952,750 | 4/1976 | Mirowski et al. |
| 4,223,678 | 9/1980 | Langer et al. ................... 128/419 D |
| 4,295,474 | 10/1981 | Fischell ............................. 128/697 |
| 4,296,755 | 10/1981 | Judell ............................. 128/419 D |
| 4,716,903 | 1/1988 | Hansen et al. |
| 4,791,936 | 12/1988 | Snell et al. ......................... 128/697 |
| 4,819,643 | 4/1989 | Menken . |
| 4,913,146 | 4/1990 | DeCote, Jr. . |
| 4,940,054 | 7/1990 | Grevis et al. . |
| 5,179,945 | 1/1993 | Van Hofwegen et al. .... 128/419 D |

FOREIGN PATENT DOCUMENTS 8823170  3/1989  Australia ..................... A61N 1/362

OTHER PUBLICATIONS

D. Williams et al., "Automatic Implantable Cardioverter–Defibrillator-Related Complications", JACC, vol. 15, No. 2, Abstracts, p. 55A (Feb. 1990.55A).

G. H. Bardy et al., "Failure of the Automatic Implantable Defibrillator to Detect Ventricular Fibrillation", The Amer. Journal of Cardiology, vol. 58, pp. 1107–1108 (Nov. 15, 1986).

Primary Examiner—William E. Kamm
Assistant Examiner—Scott M. Getzow
Attorney, Agent, or Firm—Gottlieb, Rackman & Reisman

[57] ABSTRACT

An improved implantable pacemaker/defibrillator device in which a first and relatively simplistic technique is employed to detect an abnormal heart rhythm and a second more precise algorithm is utilized for the more difficult problem of confirming the arrythmia. Since the complex, higher power consuming device is utilized only for confirmation, overall power consumption is minimized. Optionally, the precise algorithm may be utilized periodically to adjust the sensitivity of the detection circuitry.

25 Claims, 3 Drawing Sheets

CARDIOVERTING DEFIBRILLATING DEVICE WITH OFF-LINE ECG ANALYSIS

This is a continuation-in-part of copending application Ser. No. 07/851,624 filed on Mar. 16, 1992, now abandoned.

TECHNICAL FIELD OF THE INVENTION

This invention relates to arrythmia reverting devices and, more particularly, to an improved method and apparatus for detecting an arrhythmia and providing electrical therapy to shock the heart back to normal sinus rhythm.

DESCRIPTION OF THE PRIOR ART

Many advances have recently been made in implantable pacemaker/defibrillator devices which allow these devices to recognize an abnormally functioning heart and to provide therapy in the form of one or more electrical discharges into the heart in order to shock the heart back to normal sinus rhythm. One example of such a device is disclosed in U.S. Pat. No. 3,952,750 issued to Mirowski, et al.

Despite such advances, there is still room for improvement in this field. In particular, the device must be capable of accurately identifying the presence of an abnormal heart rhythm; e.g., ventricular tachyrhythmia, ventricular fibrillation, etc. Moreover, not only is it imperative that the device recognize the presence of the arrhythmia accurately, but it is essential that the arrhythmia be confirmed prior to aggressive electrical therapy being delivered to the heart. Specifically, there is normally a period of time of up to 30 seconds from the time a ventricular tachyrhythmia or fibrillation is detected until the shock is delivered to the heart. The arrythmia could, for example, spontaneously revert during this time. The presence of the arrythmia must therefore be accurately confirmed at the end of this period of time, just prior to delivery of the electrical therapy.

Although it is difficult to detect and confirm arrythmias, the confirmation step is particularly troublesome when compared with initial detection. This is because large random variations in the magnitude of the ECG signal occur during the time period between detection and confirmation. If the amplitude of the ECG signal produced by the abnormal heartbeat decreases by too much, the device may determine that the arrythmia has reverted when it really hasn't. Conversely, if the ECG amplitude of the normal heartbeat increases even though the arrythmia reverts, the device will over-sense and confirm the presence of an arrythmia when, in fact, the arrythmia is no longer present.

Additionally, even in the initial detection step, problems with changing body resistance, lead characteristics, etc., hinder accurate measurements of ECG signals. Any error in the detection or confirmation of an abnormal heart rhythm results in either unnecessary electrical shock being delivered to the heart, or electrical therapy not being delivered when such therapy is needed.

It can be appreciated from the above that the need to accurately detect and confirm arrhythmias requires accurate and adaptive sensing and measurement of ECG signals. Indeed, the Williams et al. article, entitled "Automatic Implantable Cardioverter-Defibrillator Related Complications," *Journal of the American College of Cardiology*, Vol. 15, No. 2, abstract, page 55A February 1990, reports that 0.6% of deaths associated with implantable cardioverter defibrillators were due to sensing failure, and that 4.9% of non-fatal complications were due to over-sensing. More simply put, the implantable device must be capable of (1) accurately detecting an arrythmia even though the measured ECG signal resulting from such an arrythmia may be larger or smaller than the ECG signal from a previous arrythmia; and (2) accurately confirming an arrythmia even though the ECG signal may greatly and rapidly vary in amplitude from the time of detection until confirmation.

One technique for addressing the second of the above problems is described in U.S. Pat. No. 4,940,054 entitled "Apparatus and Method for Controlling Multiple Sensitivities in an Antitachyrhythmia Device", to Richard Grevis and Norma Gilli. In this device, the gain of the sensing system is increased prior to the confirmation point. This increase in gain increases the probability of confirmation. A potential problem with this arrangement is that if spontaneous reversion occurs after detection and prior to confirmation, but the normal sinus rhythm produces a signal which is slightly greater than normally expected, the detector may confirm the arrhythmia, even though such arrhythmia is no longer present. Such false confirmation results in unnecessary, and indeed possibly harmful, electrical shocks being delivered to the heart.

An additional prior art system addressed to the above problems is described in U.S. Pat. No. 4,819,643 to J. Menken. The Menken arrangement provides for automatic gain control of the signal being utilized to detect and confirm an arrhythmia. As the amplitude of the ECG signal varies, the gain of an amplifier detecting the ECG signal varies inversely. Thus, decreases in ECG amplitude are compensated for by increases in gain. However, even the Menken system does not fully solve the problem, as explained by Bardy et al. in the article, "Failure of the Automatic Implantable Defibrillator to Detect Ventricular Fibrillation", *American Journal of Cardiology*, Vol. 58, Nov. 15, 1986, pp. 1107–1108. Specifically, even though automatic gain control is present in the device, the gain cannot be adjusted fast enough to follow rapid fluctuations in the amplitude of electrocardiac responses which occur between detection and confirmation. Such rapid fluctuations are often present, for example, during ventricular fibrillation (VF). Indeed, Bardy et al. conclude the article by stating that there is a "limitation of an arrhythmia-sensing algorithm that depends on automatically adjusting the gain of an electrical signal to detect VF while that signal may be changing rapidly in magnitude".

In addition to the above systems, there are prior arrangements that have attempted to utilize digital storage techniques in conjunction with implantable pacing systems, although none are directed to the sensitivity adjustment problem. U.S. Pat. No. 4,716,903 to Hansen et al. ("Storage in a Device Memory") discloses an implantable device which utilizes digital storage and a compression algorithm so that a representation of an ECG signal may be stored and analyzed at a later time by a physician. Australian Pat. No. 8,823,170, issued to H. Lagergren and entitled "Pacemaker System", teaches the storage of an ECG signal on a rolling basis so that a finite window of samples is always available in memory. Finally, U.S. Pat. No. 4,913,146 issued to R. Decote, Jr. ("Cardiac Sense Amplifier with Pattern Recognition Capabilities") discloses a device which processes a filtered ECG signal by utilizing a microprocessor. From the processed and filtered signal, a set of cardiac waveform descripters is derived. These waveform descripters may then be stored in memory as a template. When another template taken at a later time differs from the stored template by a sufficient amount, it is determined that an arrhythmia or other abnormality is present.

SUMMARY OF THE INVENTION

The above problems of the prior art are overcome and numerous other advantages achieved in accordance with the present invention which relates to an improved apparatus for processing stored samples of an electrocardiogram (ECG) signal to more accurately detect and reconfirm the presence of an arrhythmia. Specifically, upon detection of an arrythmia by a relatively simple detection means, data samples representing a portion of an ECG signal are stored in random access memory (RAM). The portion of the ECG signal stored is large enough to contain several R-waves, i.e., at least two. A second and more precise algorithm operates on the stored samples utilizing advanced signal processing techniques which are well known in the art. The second algorithm is used to confirm the arrythmia just prior to delivering electrical shock to the heart. By utilizing a conventional technique to detect the arrythmia, power is conserved. The more precise and complex confirmation algorithm, which requires higher power consumption, is utilized only to confirm the arrythmia after detection, thereby minimizing overall power consumption.

In another embodiment, the signal processing algorithm may also be utilized to adjust the sensitivity of the arrythmia detector. For example, once a day, the algorithm can be utilized to count heartbeats for a period of time while the arrythmia detector does the same. If the arrythmia detector detects fewer heartbeats than the algorithm, the sensitivity of the arrythmia detector is increased. Conversely, the sensitivity of the arrythmia detector is decreased if it detects more heartbeats than the signal processing algorithm. Thus, the algorithm is utilized to improve operation of the arrythmia detector.

Advantageously, the confirmation algorithm is more precise than the conventional detection means in that the algorithm can better adjust for rapid signal amplitude variations, variations in lead resistance, etc. By storing a digital representation of a plurality of R-waves and performing a detailed analysis, not necessarily in real-time, a much more accurate determination of ECG activity can be obtained than that obtained from a conventional detection technique.

DETAILED DESCRIPTION OF THE PREFERRED EMBODIMENTS

Figure 1:
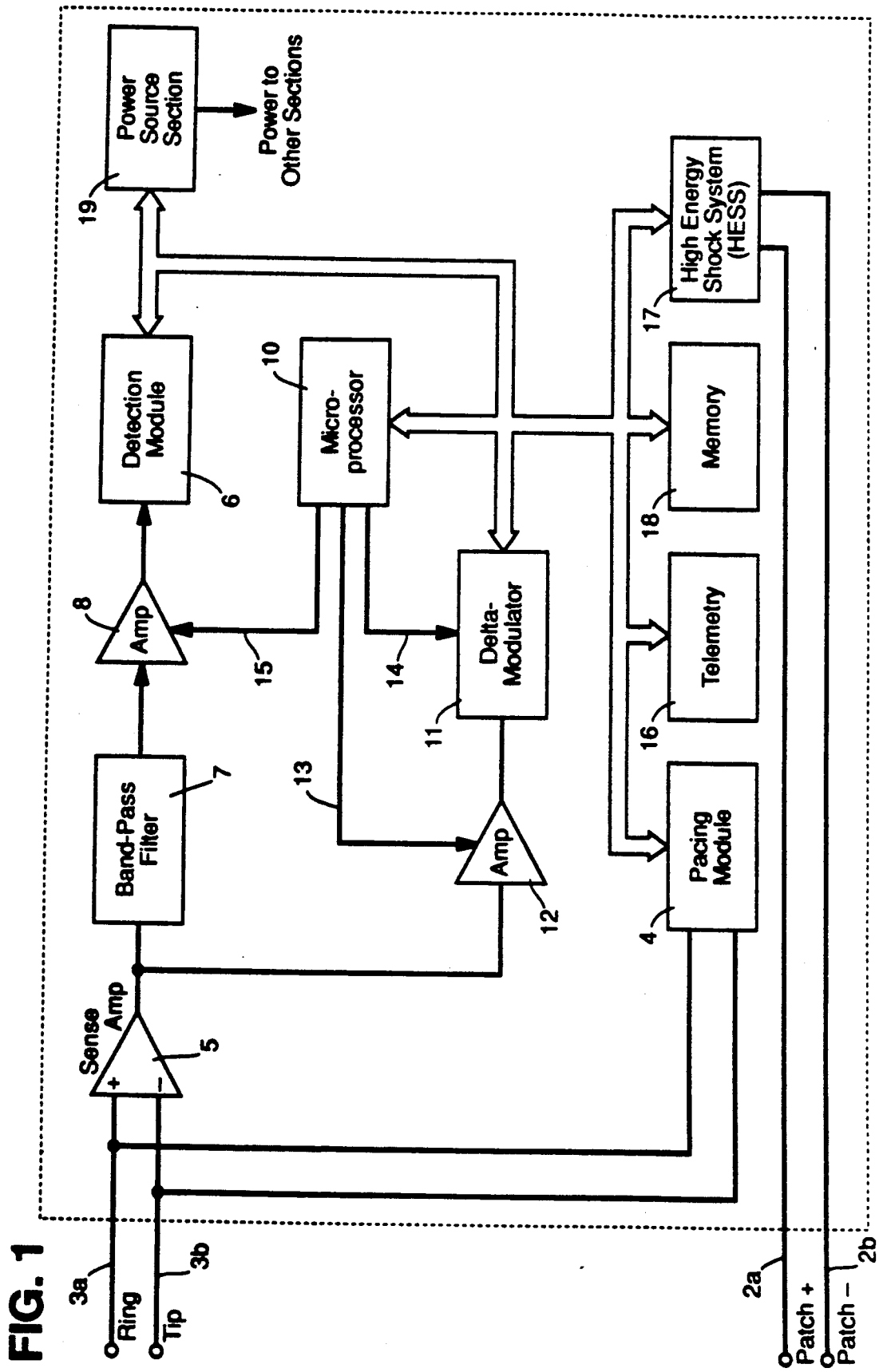
FIG. 1 is a block diagram of a microprocessor based system for implementing the method of the present invention.

FIG. 1 is a block diagram of an implantable pacing device in accordance with the invention. The device includes numerous amplifiers, detection modules, and other electronic components to be described hereafter. Additionally, the pacing device includes a high-energy shock system (HESS) 17 for delivering defibrillating shocks to the heart when necessary.

Sensing amplifier 5 receives signals from conductors 3a and 3b, and amplifies the difference therebetween. This difference is processed by band-pass filter 7 to remove slow drifts and attenuate the amplitude of T waves in the signal from the sensing and pacing leads. The band-pass-filtered signal is then supplied to selectable gain amplifier 8, the gain of which is controlled by microprocessor 10 in accordance with the result dictated by a signal processing algorithm.

Amplifier 12 is also arranged to receive signals from conductors 3a and 3b through sensing amplifier 5. Amplifier 12 provides the amplified signal to delta modulator 11 which samples the signal and provides a plurality of digital samples to microprocessor 10. A finite window of samples is provided for use by microprocessor 10 in the signal processing algorithm for determining the proper gain adjustments to be made to amplifier 8 and for detecting the arrythmia. Delta modulator 11 is also utilized to provide the samples to be processed for confirmation, as described below.

The pacing system also includes conventional elements such as a pacing module 4, working memory 18, and a power source 19. Telemetry means 16 is any of a variety of well-known arrangements of circuitry for telemetrically communicating with a physician's equipment located external to the patient's body. Finally, high-energy shock system (HESS) 17 may be invoked as needed in order to provide defibrillating electrical shocks to the cardiac tissue via leads 2a and 2b if the pacing device determines that such shocks are needed.

Figure 2:
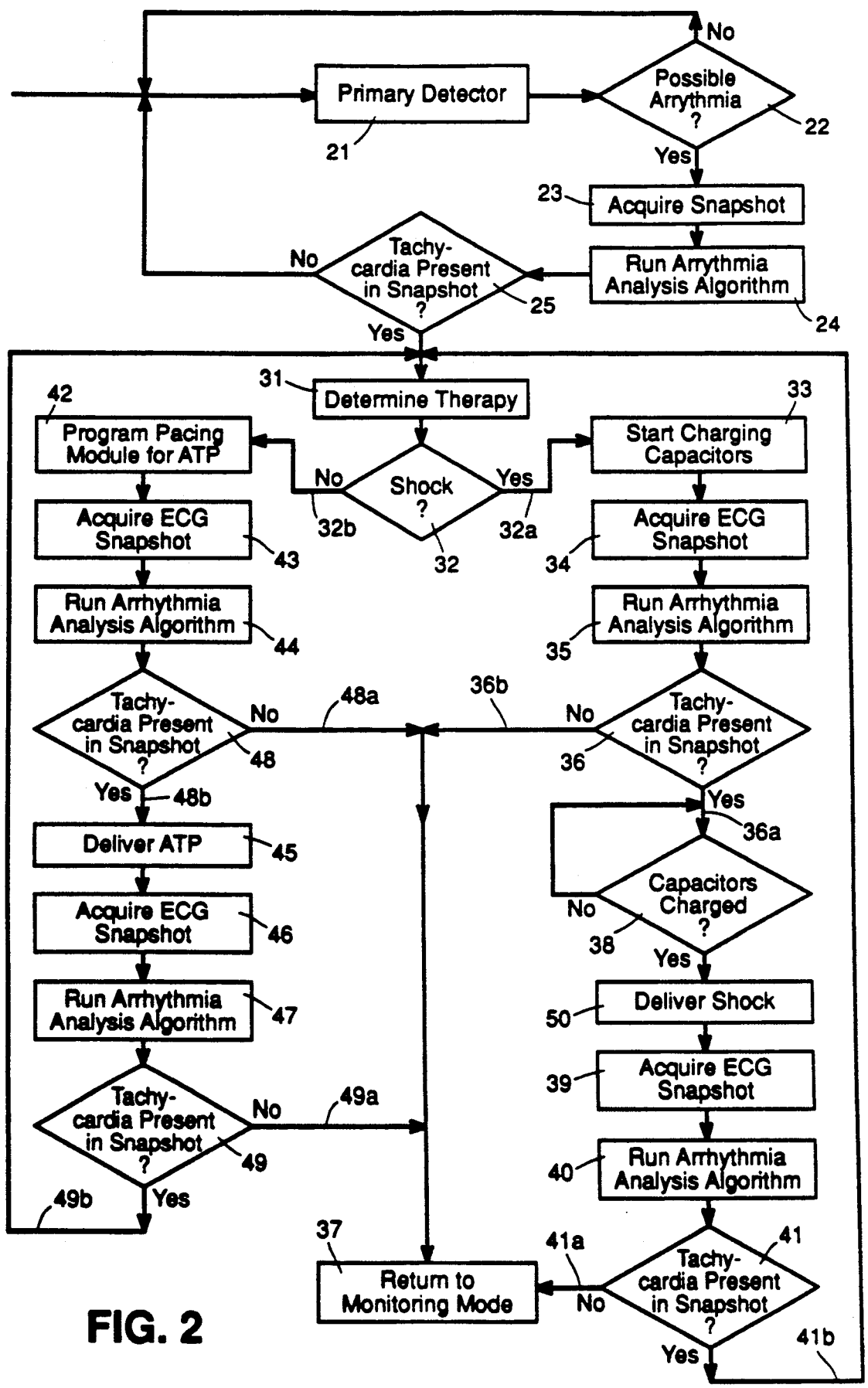
FIG. 2 is an exemplary flow diagram showing the major steps of an algorithm for implementing the present invention.

Turning now to FIG. 2, shown therein is a flow chart which may be used in programming microprocessor 10 in order to implement the invention. The following description of FIG. 2 discusses how the algorithm is utilized to confirm the arrhythmia.

During normal sinus rhythm, the system is in a monitoring state. The delta modulator 11 is not sampling ECG signals, and the shock capacitors included in the HESS are not charged. The microprocessor may optimally be put in a standby mode during this time so that power consumption may be significantly reduced.

The flow chart in FIG. 2 is entered from the monitoring state upon the detection of a possible arrhythmia at block 21 by a primary detector (not shown) in the detection module 6. The settings and algorithm used by the primary detector are selected so that the detector is very sensitive, detecting all arrhythmias and numerous rhythms that are benign and do not need therapy. At decision block 22, a decision is made as to whether or not the rhythm detected as possible arrhythmia. If it is not a pssible arrhythmia, the program loops back to the input of block 21. If the rhythm detected by the primary detector 21 is a possible arrhythmia, a "snapshot" of the electrocardiogram is acquired at block 23 and stored in the RAM memory of the microprocessor 10, and an arrhythmia analysis algorithm is initiated at block 24. The length of the snapshot portion of the electrocardiogram is determined by information from the primary detector. The memorized portion of the ECG signal is also stored in a separate part of microprocessor memory for later recall by, and display to, operators of the apparatus. In block 24, the snapshot is analyzed by the microprocessor and software algorithms as a secondary detector to determine whether a true arrhythmia is present. This arrhythmia analysis or secondary detection algorithm is significantly more specific than the primary detector. Following the analysis of the snapshot in block 24, a decision is made at block 25 regarding whether or not an arrhythmia is present in the snapshot. If no arrhythmia is present in the snapshot, the program loops back to the input of the primary detector block 21, returning the program to a monitoring state. If an arrhythmia is present in the snapshot, the program proceeds to block 31. The proper therapy required to end the arrhythmia and revert the heart to normal sinus rhythm is determined in accordance with a therapy strategy algorithm at block 31. For example, the therapy strategy algorithm may determine the parameters for the train of pacing impulses to be delivered to the heart, or the required energy for reverting the arrhythmia. Proper determination of the therapy to be delivered depends upon, among other things, the nature of the arrhythmia detected by detection module 6 of FIG. 1. A variety of well-known therapy strategies and algorithms are presently in use; the particular algorithm utilized may vary from system to system.

If the therapy strategy algorithm determines at decision point 32 that a defibrillating shock should be delivered to the heart, block 33 is entered via branch 32a and the defibrillation capacitors begin to charge. As the defibrillation capacitors begin to charge, the delta modulator 11 is activated and begins providing samples of electrocardiac activity for a predetermined time window. The time window is long enough to include multiple R-waves, and is represented in FIG. 2 by block 34, labelled "acquire ECG snapshot".

After an ECG snapshot is acquired, i.e., the predetermined time window has elapsed, all samples from delta modulator 11 are input to the arrhythmia analysis algorithm and processed accordingly as indicated in block 35. There are two main parts to the arrhythmia analysis algorithm. The first part extracts significant events from the sampled signal, as may be done utilizing the method given in co-pending U.S. patent application Ser. No. 851,524, filed Mar. 16, 1992. It is emphasized, however, that any method of extracting events may be utilized without violating the scope of the invention.

The second part of the algorithm is utilized to determine the present cardiac rhythm. This may be done utilizing a variety of straightforward techniques. For example, if N events are detected as represented by the samples in the window of time of the ECG snapshot and the snapshot is Y units wide, it can be determined that an event is occurring every Y/N time units. As cardiac rhythm increases toward tachyrhythmia and ultimately to VF, Y/N becomes smaller. Accordingly, it can be determined whether particular arrhythmias are present by comparing Y/N to a predetermined set of thresholds.

It is preferable that the ECG snapshot be acquired and analyzed at such time that the analysis is completed just prior to completion of the charging of the shock capacitors. For example, if the shock capacitors take 30 seconds to charge and the ECG snapshot takes 4 seconds to acquire and 10 seconds to analyze, then the system should begin acquiring the ECG snapshot just a little less than 16 seconds after the arrhythmia is detected. In that case, the 14 seconds for acquisition and analysis will conclude 30 seconds after detection. Since the shock capacitors begin charging immediately after detection and take 30 seconds to charge, the system will be fully charged just when the arrythmia is confirmed.

After the arrhythmia analysis algorithm is run, a decision is made at decision point 36 as to whether or not an arrhythmia is present in the analyzed ECG snap-shot. For example, the arrhythmia analysis algorithm could determine that ventricular tachycardia is present, ventricular fibrillation, etc.

If the arrhythmia analysis algorithm determines that normal sinus rhythm is present in the ECG snap-shot, the tachyrhythmia is deemed to have spontaneously reverted and processing proceeds along decision branch 36b and returns to the monitoring mode in which the system existed prior to the detection of an arrhythmia, as shown at block 37. Optionally, the episode may be logged in memory for later analysis by the physician who may read the data from memory telemetrically. Furthermore, prior to returning to monitoring mode, any charge on the shock capacitors is dissipated, the HESS is placed in the off state, and all elements return to a low power consumption mode.

If the presence of tachyrhythmia is confirmed at decision point 36, processing proceeds along branch 36a to decision point 38. Decision point 38 is, in effect, a simple programming loop which continues to cycle around upon itself thereby allowing time for the shock capacitors to charge. After such charge has occurred, control is transferred to block 50 which delivers a shock to the heart in an attempt to revert the tachyrhythmia. After the shock is delivered, control is transferred to block 39 where the processor acquires another ECG snapshot. After this snapshot is acquired, the arrhythmia analysis algorithm is repeated at block 40 in order to determine whether the tachyrhythmia has reverted. Decision point 41 then transfers control to monitoring mode block 37 via branch 41a if the tachyrhythmia has reverted. The steps executed in monitoring mode 37 are the same as those previously described, e.g., lower power consumption, etc. If the analysis algorithm run at block 40 indicates that the shock delivered at block 50 was not successful in reverting the tachyrhythmia, then decision point 41 transfers control back up via branch 41b to block 31 and the process of formulating a therapy strategy thereby repeats.

Having examined the sequence of steps executed when it is determined at decision point 32 that a shock should be delivered to the heart, the following discussion addresses the sequence of steps executed when it is determined that no shock should be delivered but, rather, that antitachyrhythmia pacing (ATP) should be administered instead. In this situation, branch 32b from decision point 32 is taken, and the proper ATP parameters are programmed into pacing module 4 of FIG. 1 as shown at block 42. Before delivering ATP to the heart, blocks 43 and 44 acquire and analyze an ECG snapshot for the purpose of reconfirming the presence of the tachyrhythmia. Decision point 48 returns the system to the monitoring mode via branch 48a and block 37 if the tachyrhythmia is no longer present, i.e., spontaneous reversion has occurred.

If decision point 48 confirms the tachyrhythmia, branch 48b is taken and control is transferred to block 45 in order to deliver ATP. Blocks 46 and 47 then serve to determine whether or not the arrhythmia is still present, as previously described for block 39 and 40. Finally, decision point 49 returns the system to the monitoring mode via branch 49a and block 37 if the ATP has been successful in reverting the arrhythmia, but transfers control to block 31 via branch 49b for re-administering therapy if the ATP has been unsuccessful.

Figure 3:
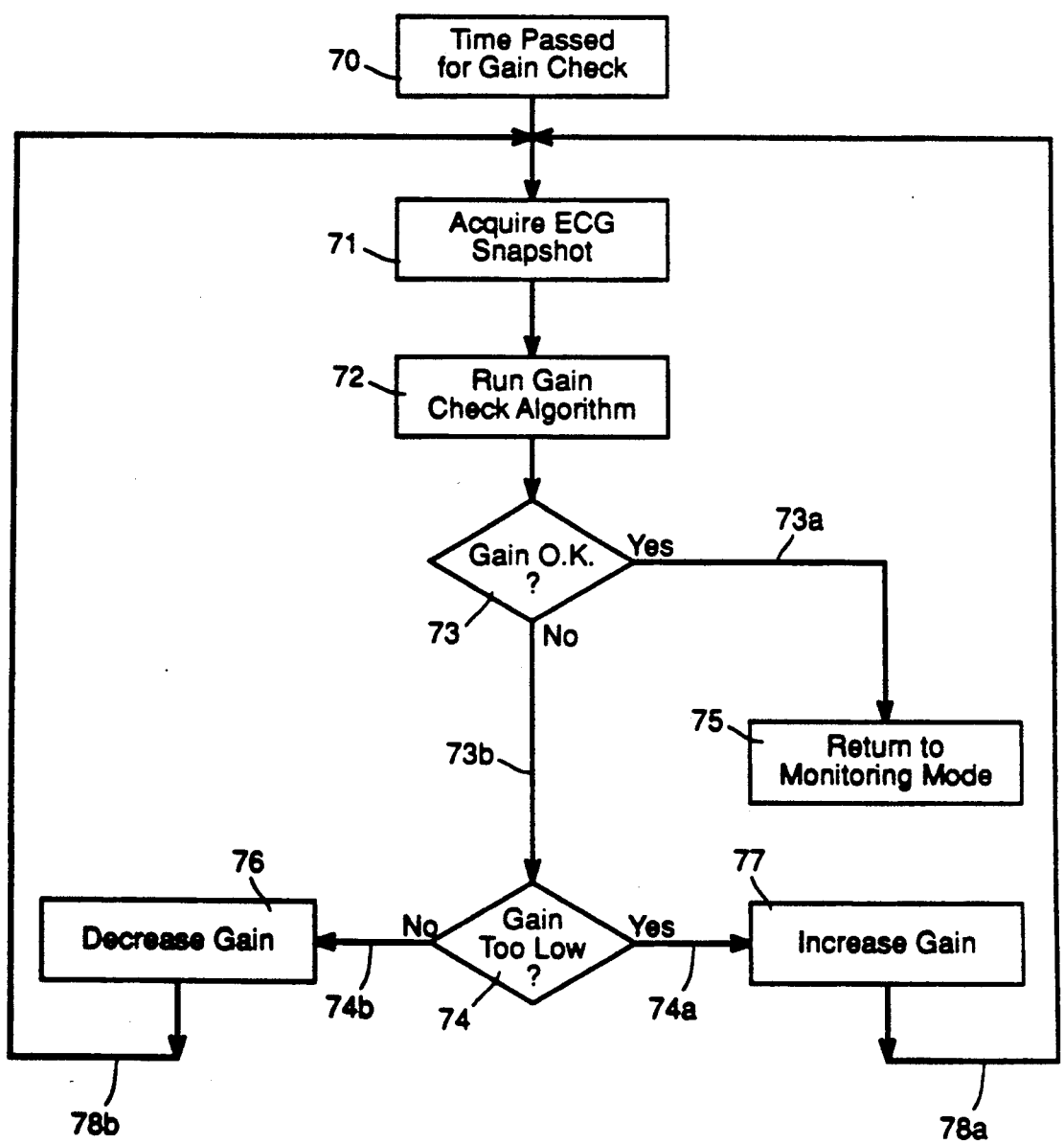
FIG. 3 is an additional flow diagram showing other portions of a preferred algorithm.

FIG. 3 is a flow diagram of a gain adjustment algorithm which is utilized to adjust the gain of selectable gain amplifier 8 of FIG. 1 or, equivalently, the sensitivity of the arrythmia detector 6. The algorithm shown by the flow chart in FIG. 3 is run at regular infrequent intervals, e.g., once a day or less, and is used to allow the non-real-time signal processing to assist in adjusting subsequent initial detection of an arrythmia. Of course, the actual interval used could be selected by the physician and even varied using telemetric means.

When a timer (not shown) indicated that the proper amount of time has passed for a gain adjustment process to occur, the system will first check to assure that no type of therapy, such as that described with reference to FIG. 2, is currently being delivered. Thus, the gain adjustment process can only be invoked from the monitoring mode. The gain adjustment process is entered at block 70 of FIG. 3 by a signal from the timer. Control is transferred to block 71 which acquires an ECG snapshot in the manner previously described. The delta modulator used to acquire the ECG snapshot for gain adjustment of amplifier 8 may be the same delta modulator as previously described. After an ECG snapshot is acquired, control is transferred to block 72 in order to run a gain check algorithm to determine whether the gain in amplifier 8 must be increased or decreased. One example of a gain check algorithm, although quite simplistic, is to simply count the number of heartbeats detected by the detection module 6. If the therapy strategy algorithm detects many more heartbeats than the detection module 6, it is assumed that the gain of the detection module 6 is too low. If there are many more detects from the detection module, a decision is made that the gain of the detection module is too high.

The algorithm used to extract events from the snapshot for the purpose of gain verification may be the same algorithm used for arrhythmia analysis. If decision point 73 determines the gain of amplifier 8 is acceptable, it transfers control to block 75 via branch 73a and the system returns to the monitoring mode. If, however, the gain is not correct, control is transferred to decision point 74 via branch 73b. Decision point 74 then increases or decreases the gain accordingly, utilizing branch 74a, block 77 and branch 78a in connection with increasing the gain, and utilizing branch 74b, block 76 and branch 78b in connection with decreasing the gain.

The gain of amplifier 8 may be increased or decreased in fixed steps. Each time it is determined that the gain should be raised or lowered, the gain is increased or decreased by one step. The steps are made small enough so as to avoid an unstable system which oscillates about the target gain point but which never stabilizes.

It is noted that the details of spectrum analysis, digital signal processing, and other related fields have not been described in detail herein. However, any of the multitude of algorithms available may be utilized in analyzing and extracting information from an ECG snapshot. For example, the original signal from which the delta values were derived could be reconstructed and a correlation used to match the resulting ECG to a template. A template could be one of a library of templates corresponding to different rhythms which may have similar rates but which respond most favorably to different electrotherapies. This would allow different therapies to be delivered for arrhythmias which have similar rates but different shapes. Other techniques may be used on the ECG snap-shots, such as Fourier analysis, noise filtering, etc. The well-known text, *Digital Signal Processing*, by Oppenheim and Schafer (Prentice Hall, Englewood Cliffs, N.J.), describes a variety of still other signal processing techniques which may be utilized with the present invention. Not only can the signals be processed in non-real-time, but they may also be processed out of order.

What is claimed is:

1. Apparatus for administering electrotherapy to a patient's heart to restore a normal heart rhythm comprising:
   an unsophisticated primary detector means for detecting, with a first degree of precision, possible abnormalities in a patient's heart rhythm;
   a sophisticated secondary detector means for analyzing the heart rhythm and more precisely identifying abnormalities therein, said secondary detector means being generally inactive in regard to detecting and analyzing abnormalities in the heart rhythm in the absence of a detection of a possible abnormality by said primary detector means;
   memory means within said secondary detector means for storing a portion of an ECG signal;
   means responsive to the detection of a possible abnormality in the heart rhythm by said primary detector means for activating said secondary detector means and for causing at least a portion of said ECG signal to be stored in said memory means, said secondary detector means being constructed and arranged to analyze said stored portion of said ECG signal with a second degree of precision significantly higher than the first degree of precision exercised by said primary detector means in order to confirm said rhythm abnormality; and
   means responsive to confirmation of said rhythm abnormality by said secondary detector means for delivering appropriate electrocardiac therapy to the heart.

2. Apparatus according to claim 1, wherein said secondary detector means includes a microprocessor that employs digital processing techniques for analyzing said stored portion of said ECG signal.

3. Apparatus according to claim 2, further including means for storing a digital representation of a sufficiently large enough portion of said ECG signal for said portion to contain at least 2 R-waves therein; and means for processing said stored digital representation in non-real time to confirm said rhythm abnormality.

4. Apparatus according to claim 1, further including means for initiating analysis of said stored signal by said secondary detector means after said portion of said signal has been stored in said memory means.

5. Apparatus according to claim 1, further including means for comparing selected cardiac events detected by said primary detector means during a predetermined time period to corresponding cardiac events detected by said secondary detector means during said predetermined time period; and means responsive to said comparison for modifying at least one property of said primary detector means in order to optimize its performance relative to said secondary detector means.

6. Apparatus according to claim 5, further including means for activating said comparing means and said modification means at predetermined intervals to maintain said primary detector means at an optimum performance level.

7. Apparatus according to claim 1, further including amplifying means having an adjustable gain and being coupled to said primary detector means for amplifying an ECG signal of the patient's heart rhythm and inputting said amplified signal to said primary detector means; means for comparing selected cardiac events detected by said primary detector means during a predetermined time period to corresponding cardiac events detected by said secondary detector means during said predetermined time period; and means responsive to said comparison for adjusting the gain of said amplifying means in order to optimize the performance of the primary detector means relative to said secondary detector means.

8. Apparatus according to claim 7, further including means for activating said comparing means and said gain adjusting means at predetermined intervals to maintain said primary detector means at an optimum performance level.

9. Apparatus according to claim 1, wherein said primary detector means includes means for determining the length of the portion of the ECG signal that is to be stored in said memory means.

10. Apparatus according to claim 1, wherein said memory means includes first and second memories, wherein said portion of said ECG signal is stored in each of said first and second memories, wherein said portion of said ECG signal stored in said first memory is analyzed by said secondary detector means, and wherein said portion of said ECG stored in said second memory is preserved for later recall by, and display to, an operator of said apparatus.

11. Apparatus according to claim 1, wherein said therapy delivery means requires a predetermined delay period following the initial detection of an abnormality in order to prepare for delivery of therapy to the heart, and wherein said secondary detector means is constructed and arranged to confirm that the abnormality is still present immediately prior to the delivery of electrical therapy to the heart.

12. Apparatus according to claim 1, wherein said secondary detector means is controlled by an algorithm that operates on the portion of said ECG signal that is stored in said memory means, and wherein the power consumed by said secondary detector during operation of said algorithm is significantly greater than the power consumed by said primary detector when the latter is detecting possible abnormalities in the patient's heart rhythm.

13. A method of administering electrotherapy to a patient's heart to restore a normal heart rhythm comprising:
providing an unsophisticated primary detector for detecting, with a first degree of precision, possible abnormalities in a patient's heart rhythm, and a sophisticated secondary detector for analyzing the heart rhythm and more precisely identifying abnormalities therein, said secondary detector being generally inactive in regard to detecting and analyzing abnormalities in the heart rhythm in the absence of a detection of a possible abnormality by said primary detector, said secondary detector including a memory for storing a portion of and ECG signal;
in response to the detection of a possible abnormality in the heart rhythm by said primary detector, activating said secondary detector and storing at least a portion of said ECG signal in said memory;
analyzing said stored portion of said ECG signal in said secondary detector with a second degree of precision significantly higher then the first degree of precision exercised by said primary detector in order to confirm said rhythm abnormality; and
in response to confirmation of said rhythm abnormality by said secondary detector, delivering appropriate electrocardiac therapy to the heart.

14. A method according to claim 15, wherein said analyzing step includes a sub-step of employing digital processing techniques for analyzing said stored portion of said ECG signal.

15. A method according to claim 14, including the further step of providing said secondary detector with an algorithm that operates on the portion of said ECG signal that is stored in said memory, and wherein the power consumed by said secondary detector during operation of said algorithm is significantly greater than the power consumed by said primary detector when the latter is detecting possible abnormalities in the patient's heart rhythm.

16. A method according to claim 14, wherein said step of storing said portion of said ECG signals in memory includes the sub-step of storing a digital representation of a sufficiently large enough portion of said ECG signal for said portion to contain at least 2-R-waves therein; and further including the step of processing said stored digital representation in non-real time to confirm said rhythm abnormality.

17. A method according to claim 16, including the further step of delaying said storing and processing steps sufficiently such that said processing step is completed at approximately the same time that it is appropriate to shock the patient's heart in order to revert the abnormality.

18. A method according to claim 13, further including the step of initiating analysis of said stored signal by said secondary detector after said portion of said signal has been stored in said memory means.

19. A method according to claim 13, further including the steps of comparing selected cardiac events detected by said primary detector during a predetermined time period to corresponding cardiac events detected by said secondary detector during said predetermined period; and, in response to said comparison, modifying at least one property of said primary detector in order to optimize its performance relative to said secondary detector.

20. A method according to claim 19, further including the step of activating said comparing and said modifying steps at predetermined intervals to maintain said primary detector at an optimum performance level.

21. A method according to claim 13, including the further steps of providing an amplifier having an adjustable gain, said amplifier being coupled to said primary detector; amplifying an ECG signal of the patient's heart rhythm; inputting said amplified signal to said primary detector; comparing selected cardiac events detected by said primary detector during a predetermined time period to corresponding cardiac events detected by said secondary detector during said predetermined time period; and, in response to said comparison, adjusting the gain of said amplifier in order to optimize the performance of the primary detector relative to said secondary detector.

22. A method according to claim 21, including the further step of activating said comparing and said gain adjusting steps at predetermined intervals to maintain said primary detector at an optimum performance level.

23. A method according to claim 13, including the further step of having said primary detector determine the length of the portion of the ECG signal that is to be stored in said memory.

24. A method according to claim 13, including the further steps of providing first and second memories in said secondary detector; storing said portion of said ECG signal in each of said first and second memories; analyzing said portion of said ECG signal stored in said first memory by said secondary detector; and, preserving said portion of said ECG signals stored in said second memory for later recall by, and display to, an operator.

25. A method according to claim 13, including the further step of having said secondary detector confirm that said abnormality is still present immediately prior to said step of delivering electrical therapy to the heart.

* * * * *